United States Patent [19]
Bischoff

[11] Patent Number: 6,096,069
[45] Date of Patent: Aug. 1, 2000

[54] MEDICAL ELECTRICAL LEAD WITH CONDUCTORS COILED AROUND AN INNER TUBE

[75] Inventor: Thomas C. Bischoff, Minneapolis, Minn.

[73] Assignee: Medtronic, Inc., Minneapolis, Minn.

[21] Appl. No.: 08/985,109

[22] Filed: Dec. 4, 1997

Related U.S. Application Data

[63] Continuation of application No. 08/579,959, Dec. 28, 1995, Pat. No. 5,766,042.

[51] Int. Cl.$^7$ ...................................................... A61N 1/05
[52] U.S. Cl. ................................................................ 607/116
[58] Field of Search ..................................... 607/116, 119, 607/122

[56] References Cited

U.S. PATENT DOCUMENTS

| | | | |
|---|---|---|---|
| 3,416,533 | 12/1968 | Fisher et al. | 607/122 |
| 4,540,236 | 9/1985 | Peers-Trevarton . | |
| 4,704,103 | 11/1987 | Stober et al. . | |
| 4,934,366 | 6/1990 | Truex et al. . | |
| 5,125,915 | 6/1992 | Berry et al. . | |

*Primary Examiner*—William E. Kamm
*Attorney, Agent, or Firm*—Reed A. Duthler; Harold R. Patton

[57] ABSTRACT

A lead which is provided with a lead body and a connector assembly which are flexible and resistant to fatigue caused by flexing of the lead relative to an associated implantable medical device to which the lead is coupled. The lead is provided with an elongated lead body with a connector assembly located at its proximal end and carrying at least two elongated conductors extending along the lead body to the connector assembly, arranges such that distal to a first point along the lead body the lead body is provided with at least two separate longitudinal lumens, each carrying at least one of the two conductors and proximal to the first point, the lead is provided with a tubular member, arranged such that the two conductors extend proximally from the first point wrapped helically around the tubular member. In a preferred embodiment, the lead carries at least three elongated conductors, and at least one of the conductors is wrapped helically around the tubular at a pitch greater than the diameter the conductors. In a more preferred embodiment, at least one conductor is wrapped helically around the tubular member at a pitch greater than the diameter of the lead body.

4 Claims, 7 Drawing Sheets

102

130

130

104

104

MEDICAL ELECTRICAL LEAD WITH CONDUCTORS COILED AROUND AN INNER TUBE

This application is a continuation of application Ser. No. 08/579,959, filed Dec. 28, 1995 now U.S. Pat. No. 5,766,042.

FIELD OF THE INVENTION

The present invention relates generally to automatic, body-implantable medical device systems, and more particularly relates to a lead locking and sealing assembly for an implantable medical device.

BACKGROUND OF THE INVENTION

Various types of electronic devices are known for which an electrical and mechanical connection must be established between a wire or other flexible conductor and an electronic component. For example, there are numerous classes of automatic, body-implantable medical device systems, such as cardiac pacemakers and defibrillators, neural stimulators, and the like, for which it is commonly necessary to establish an electrical and mechanical coupling between an insulated conductive lead and an electronic component of the system. In a typical implantable pacemaker system, one or more pacing and sensing leads are coupled at their proximal ends to a hermetically enclosed pulse generator and have their distal ends disposed in or around the patient's heart. The leads function to conduct electrical cardiac signals to sensing circuitry within the hermetic enclosure, and to convey stimulating pulses from the pulse generator to the patient's heart.

There are particularly stringent design criteria with regard to the mechanical and electrical properties of the connection between a lead and a body-implantable device. An implantable device's lead connection is preferably highly reliable, both from a mechanical and from an electrical point of view, due to the potentially serious medical implications of either mechanical or electrical failure of the lead connection. Also, any physical structure used to implement an implantable device lead connection must be biologically inert (i.e., biocompatible), and is preferably small and light-weight.

In addition, a lead connection should be capable of withstanding repeated flexing of the lead with respect to the-device itself. This consideration is one reason that implantable leads are often implemented as a coiled conductor within an elongate insulative sleeve of silicone rubber, polyurethane or the like. Such a coiled conductor configuration has been shown in the prior art to have desirable fatigue resistant characteristics. Also, a lead connection should be strong enough to resist unintended disconnection due to the various forces that may be exerted upon it throughout the time it is implanted in the human body. At the same time, however, the delicate surgical process associated with implantation of such devices makes it desirable that the lead connection be relatively simple to effectuate in the surgical environment.

SUMMARY OF THE INVENTION

The present invention is directed to a lead which is provided with a lead body and a connector assembly which are flexible and resistant to fatigue caused by flexing of the lead relative to an associated implantable medical device to which the lead is coupled. The invention accomplishes this result by means of a medical lead having an elongated lead body with a connector assembly located at its proximal end and carrying at least two elongated conductors extending along the lead body to the connector assembly, arranges such that distal to a first point along the lead body the lead body is provided with at least two separate longitudinal lumens, each carrying at least one of the two conductors and proximal to the first point, the lead is provided with a tubular member, arranged such that the two conductors extend proximally from the first point wrapped helically around the tubular member. In a preferred embodiment of the invention, the lead carries at least three elongated conductors, and at least one of the conductors is wrapped helically around the tubular at a pitch greater than the diameter the conductors. In a more preferred embodiment, at least one conductor is wrapped helically around the tubular member at a pitch greater than the diameter of the lead body.

BRIEF DESCRIPTION OF THE DRAWINGS

Numerous features of the present invention will perhaps be best appreciated with reference to a detailed description of specific embodiments of the invention, which follows, when read in conjunction with accompanying drawings, wherein.

DETAILED DESCRIPTION OF SPECIFIC EMBODIMENTS OF THE INVENTION

Figure 1:
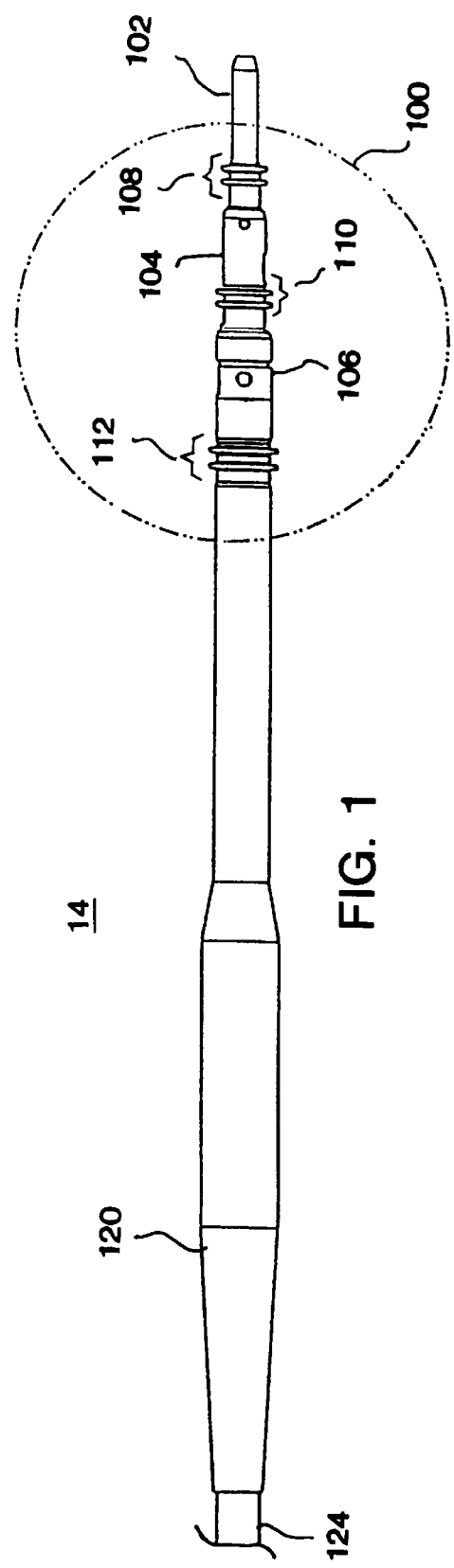
FIG. 1 is a side view of the proximal end of a lead according to the present invention.
Figure 2:
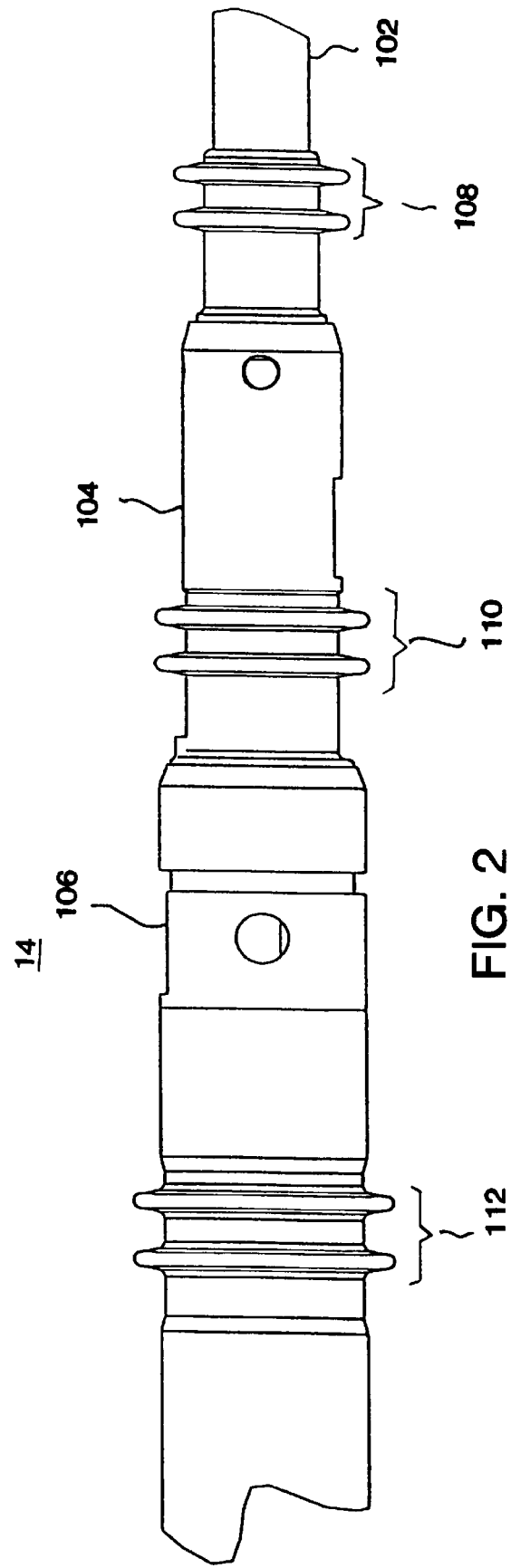
FIG. 2 is a side view of a portion of the lead shown in FIG. 1.

FIGS. 1 and 2 are side views of the proximal or terminal end of lead 14 in accordance with the presently disclosed embodiment of the invention. FIG. 2 is an enlarged side view of the portion of the proximal end of lead 14 contained within the dashed line designated 100 in FIG. 8. Although lead 14 is a tripolar lead, it is contemplated that the present invention may be advantageously practiced in the context of leads having more or fewer conductors therein, and it is believed that those of ordinary skill in the art having the benefit of the present disclosure will be readily able to do so.

As shown in FIGS. 1 and 2, lead 14 includes a connector assembly which includes three distal electrical contacts or connector electrodes, designated with reference numerals 102, 104, and 106, with connector electrode 102 being a pin electrode on the proximal end of lead 14, and electrodes 104 and 106 being ring electrodes spaced distally away from the proximal end. In the preferred embodiment, electrodes 102, 104, and 106 are made of stainless steel or another suitably conductive and biostable material.

Interspersed with electrodes 102, 104, and 106 are three sets of sealing rings 108, 110, and 112, which function to further provide a fluid-tight seal between the terminal end of lead 14 and connector block assembly 50. Sealing rings 108, 110, and 112 are preferably made of silicone rubber, polyurethane, or the like.

Figure 3:
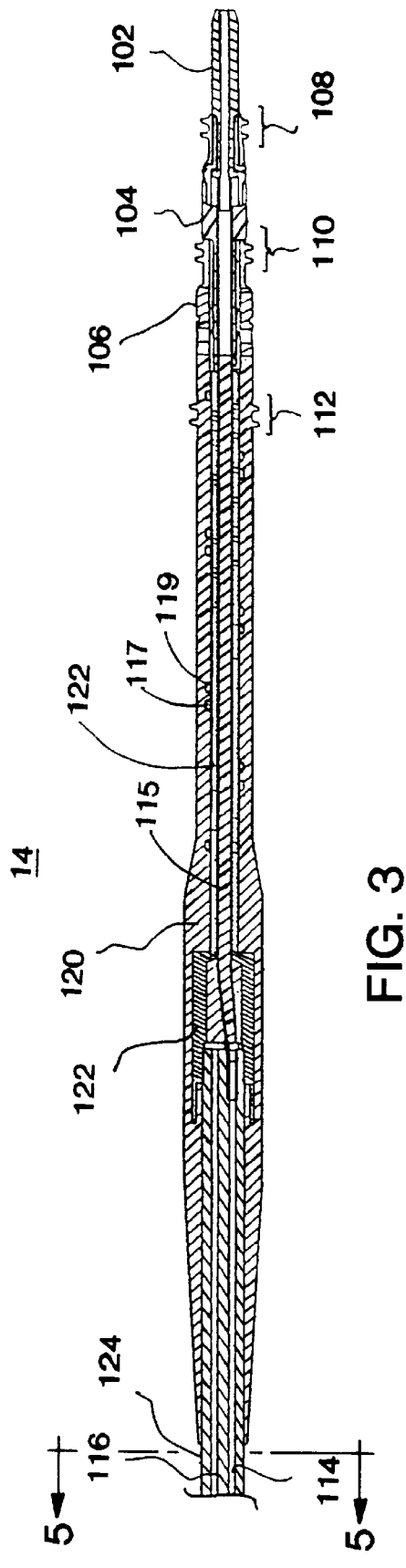
FIG. 3 is a side cross-sectional view of the proximal end of the lead from FIG. 1.
Figure 4:
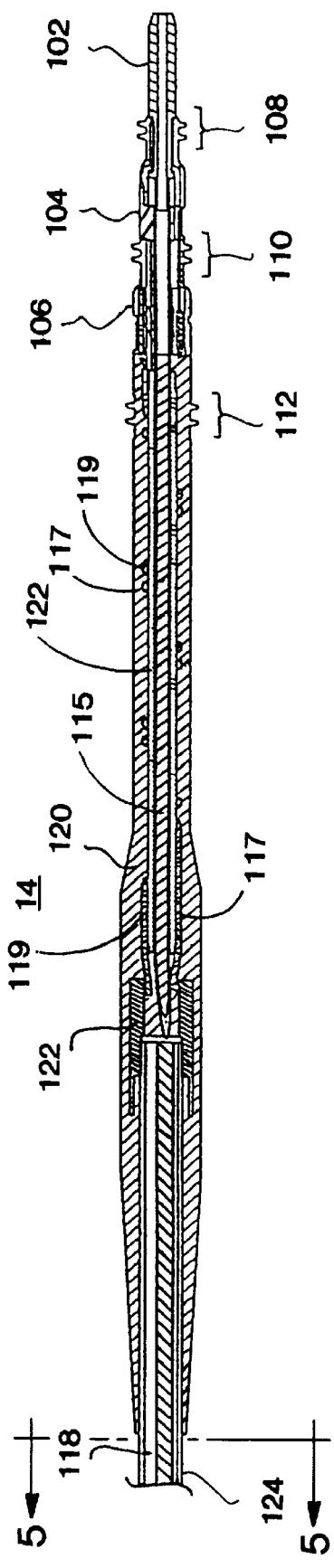
FIG. 4 is another side cross-sectional view of the proximal end of the lead from FIG. 1.
Figure 5:
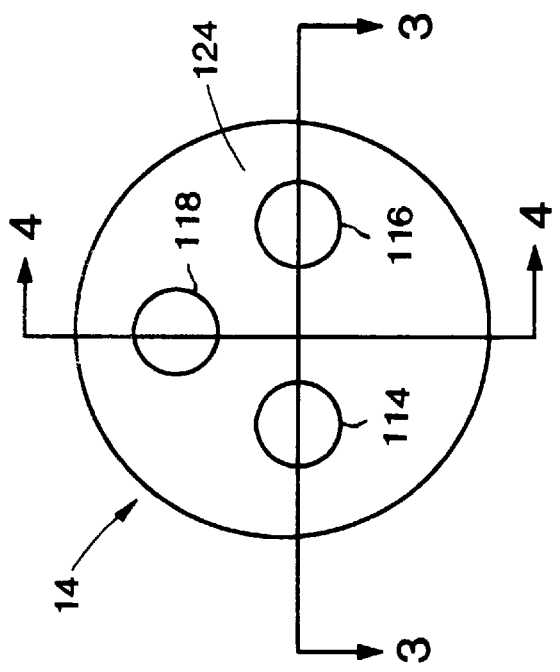
FIG. 5 is an end cross-sectional view of the lead from FIG. 1 showing the orientation of the cross-sections of FIGS. 3 and 4.

The proximal or terminal end of lead 14 is also depicted in the more detailed cross-sectional views of FIGS. 3 and 4. Lead 14 in accordance with the presently disclosed embodiment is a triaxial, multilumen lead, as shown in the cross-sectional view of FIG. 5, which also indicates the orientation of the cross-sections in FIGS. 3 and 4. In particular, lead 14 has three internal lumens 114, 116, and 118. These three lumens enable three separate 115, 117 and 119 conductors to extend along the length of lead 14.

Figure 6:
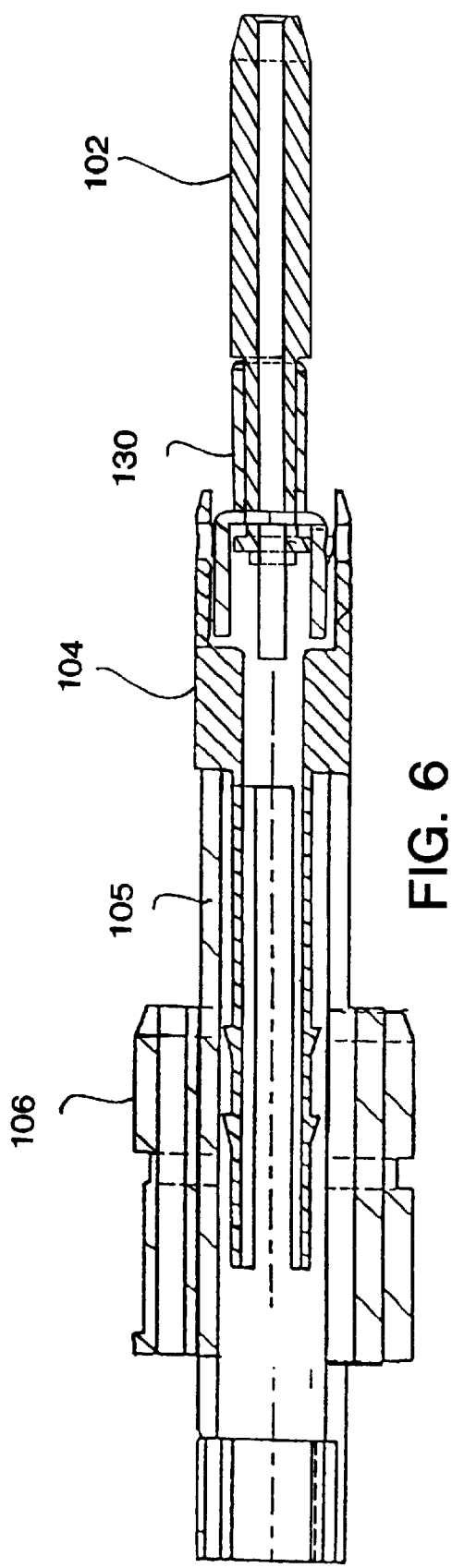
FIG. 6 is a side cross-sectional view of individual components of the terminal assembly of the lead from FIG. 3.
Figure 7:
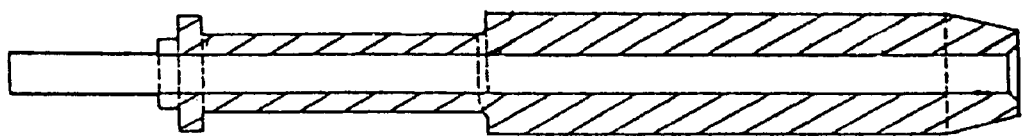
FIG. 7 is a side cross-sectional view of the pin electrode from the lead of FIG. 3.

FIG. 6 shows the various components which comprise the terminal end of lead 14. For clarity, the outer insulative sheath of lead 14, which is designated with reference numeral 120 in FIGS. 3 and 4 and preferably made of polyurethane or the like, is not shown in FIG. 6. As shown in FIGS. 3 and 4, the terminal end of lead 14 includes a connector sleeve stiffener 122, which in the preferred embodiment is made of molded 55D polyurethane. Stiffener 122 is coupled at its distal end to the multi-lumen body member of lead 14, designated with reference numeral 124 in the Figures. Conductors 115, 117 and 119 extend within the three lumens of the up to a first point 123 at which the multi-lumen lead body member 124 has its proximal termination. Thereafter, as illustrated, conductors 117 and 119 extend proximally, wound spirally around tubular stiffener 122. At is proximal end, stiffener 122 is bonded to the distal end of a polyurethane ring electrode liner 105, which is shown in FIG. 6. Liner 105 functions to insulate ring electrode 106 from ring electrode 104, which is press-fit inside liner 105. Snap-fit into the proximal end of ring electrode 104 is a molded polyurethane insert 130. Pin electrode 102, in turn, is snap-fit into insert 130.

Figure 8A:
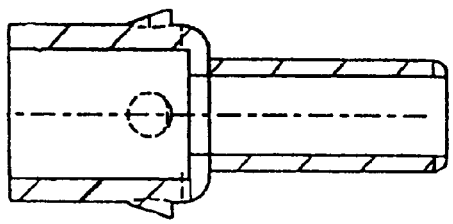
FIGS. 8a and 8b are side and end cross-sectional views, respectively, of a sense ring insert component of the lead of FIG. 3.
Figure 8B:
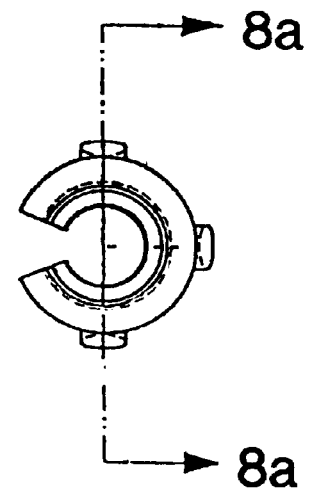
Figure 9A:
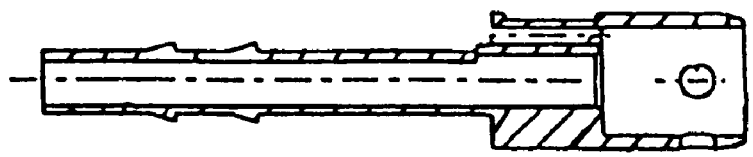
FIGS. 9a and 9b are side cross-sectional views of a ring connector electrode from the lead of FIG. 3.
Figure 9B:
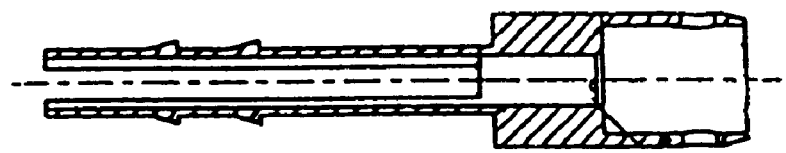
Figure 10A:
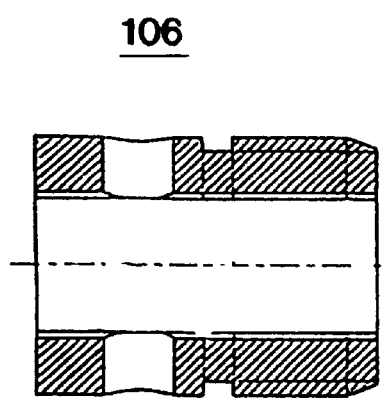
FIGS. 10a, 10b, 10c, and 10d are side cross-sectional, end cross-sectional, side cross-sectional and end cross-sectional views of another ring connector electrode from the lead of FIG. 3.
Figure 10B:
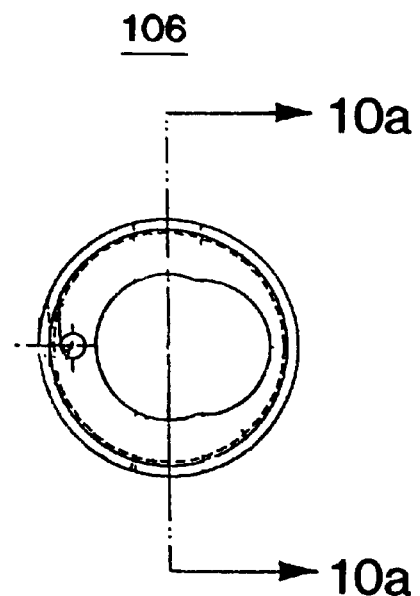
Figure 10C:
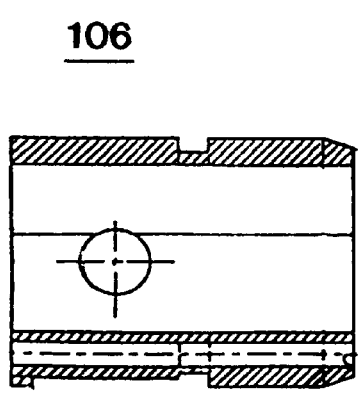
Figure 10D:
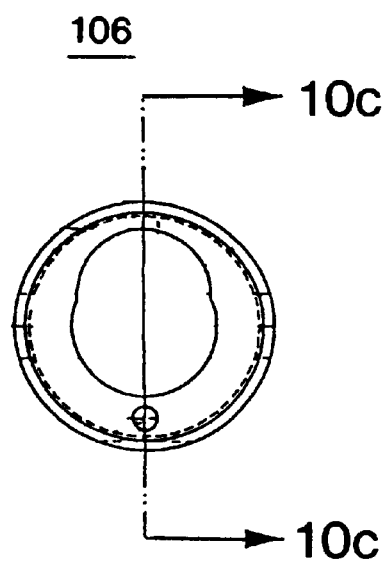
Figure 11A:
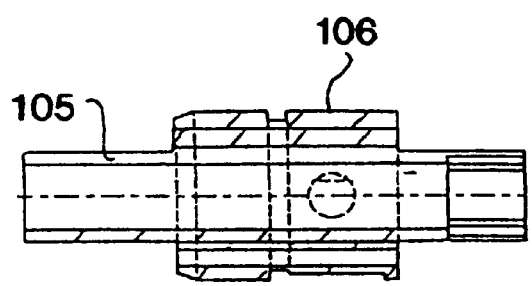
FIGS. 11a, 11b, 11c, and 11d are side cross-sectional, end cross-sectional, side cross-sectional and end cross-sectional views of a ring connector electrode assembly from the lead of FIG. 3, including the ring connector electrode from FIGS. 10a, 10b, 10c, and 10d.
Figure 11B:
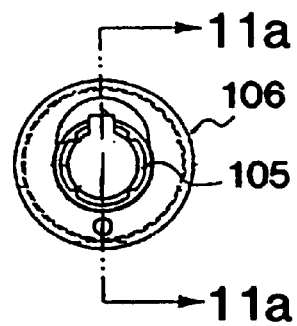
Figure 11C:
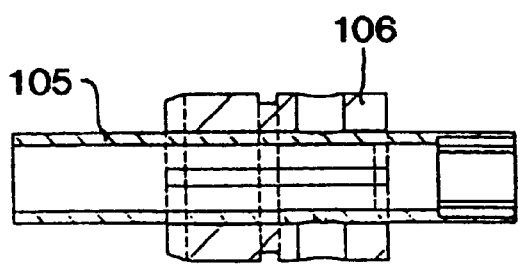
Figure 11D:
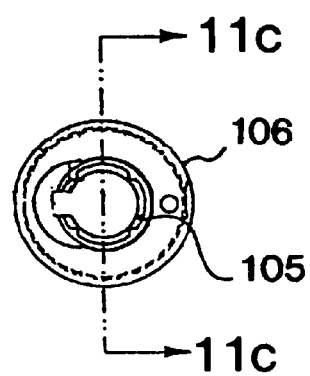
Figure 12:
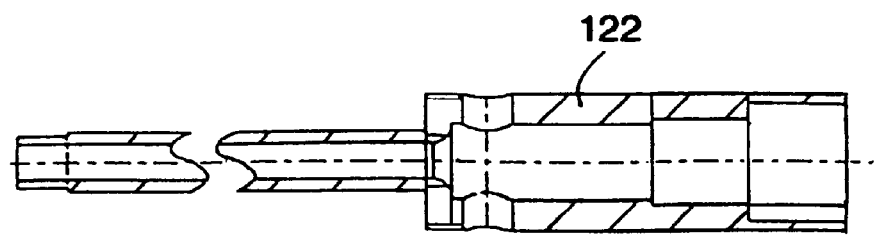
FIG. 12 is a side cross-sectional view of a stiffener component from the lead of FIG. 3.

The various components of the terminal end of lead 14—insert 130, ring electrode 104, sleeve 105, ring electrode 106 and stiffener 122—are shown in more detail in FIG. 14 (pin electrode 102), FIGS. 8a and 8b (side and end views, respectively, of insert 130), FIGS. 9a and 9b (cross-sectional views of ring electrode 104), FIGS. 10a, 10b, 10c, and 10d (side, end, side, and end cross-sectional views, respectively, of ring electrode 106), FIGS. 11a, 11b, 11c, and 11d (side, end, side, and end cross-sectional views, respectively, of the ring electrode assembly comprising ring electrode 106 and liner 105), and FIG. 12 (stiffener 122), Although numerous specific details regarding the various embodiments of the invention have been provided, it is to be understood that this has been done for the purposes of illustrating various aspects of the invention, and is not intended to be limiting with respect to the scope of the invention. It is believed that numerous alterations, substitutions, and/or modifications, including but not limited to those specifically noted herein, may be made to the disclosed embodiments without departing from the spirit and scope of the invention as defined in the following claims:

What is claimed is:

1. A medical lead having an elongated lead body with a connector assembly located at its proximal end and carrying at least two elongated conductors having diameters and extending along the lead body to the connector assembly, wherein distal to a first point distal to the connector assembly the lead body is provided with at least two separate longitudinal lumens, each carrying one of the at least two conductors, wherein proximal to the first point, said lead body comprises a tubular member extending proximally from the first point and wherein at least one of the at least two conductors extends proximally from the first point wrapped helically around the tubular member at a pitch greater than the diameter of at least one of the at least two conductors.

2. A lead according to claim 1 wherein the lead body has a diameter and the at least one conductor wrapped helically around the tubular member is wound at a pitch greater than the diameter of the lead body.

3. A lead according to claim 1 or claim 2 further comprising an outer sheath extending proximally from the first point, wherein the at least one conductor wrapped helically around the tubular member is surrounded by the outer insulative sheath.

4. A lead according to claim 3 wherein the at least one conductor wrapped helically around said tubular member is embedded in the outer insulative sheath.

* * * * *